US007841983B2

(12) United States Patent
Harada et al.

(10) Patent No.: US 7,841,983 B2
(45) Date of Patent: *Nov. 30, 2010

(54) ULTRASONIC DIAGNOSTIC APPARATUS

(75) Inventors: Akimitsu Harada, Mitaka (JP); Ryoichi Sakai, Mitaka (JP); Kozo Nakamura, Bunkyo-ku (JP); Isao Ohnishi, Bunkyo-ku (JP)

(73) Assignees: Aloka Co., Ltd., Tokyo (JP); The University of Tokyo, Tokyo (JP)

( * ) Notice: Subject to any disclaimer, the term of this patent is extended or adjusted under 35 U.S.C. 154(b) by 678 days.

This patent is subject to a terminal disclaimer.

(21) Appl. No.: 11/390,788

(22) Filed: Mar. 28, 2006

(65) Prior Publication Data

US 2006/0241447 A1 Oct. 26, 2006

(30) Foreign Application Priority Data

Mar. 31, 2005 (JP) ............................. 2005-103031

(51) Int. Cl.
*A61B 8/00* (2006.01)

(52) U.S. Cl. ..................................... 600/437; 600/438

(58) Field of Classification Search .......... 600/437–458
See application file for complete search history.

(56) References Cited

U.S. PATENT DOCUMENTS

| 5,524,636 | A | * | 6/1996 | Sarvazyan et al. .......... 600/587 |
| 5,902,240 | A | | 5/1999 | Ishii et al. |
| 6,079,255 | A | * | 6/2000 | Binnig et al. ................. 73/105 |
| 6,270,459 | B1 | * | 8/2001 | Konofagou et al. ......... 600/449 |
| 6,520,913 | B1 | * | 2/2003 | Pesavento et al. ........... 600/438 |
| 2002/0103432 | A1 | * | 8/2002 | Kawchuk ..................... 600/437 |
| 2004/0234113 | A1 | * | 11/2004 | Miga ........................ 382/128 |
| 2006/0184020 | A1 | * | 8/2006 | Sumi .......................... 600/437 |

FOREIGN PATENT DOCUMENTS

| JP | H08-131446 | 5/1996 |
| JP | 2001-309918 | 11/2001 |
| JP | 2004-298205 | 10/2004 |
| JP | 2005-152079 | 6/2005 |
| JP | 2005-160704 | 6/2005 |
| WO | WO 02/24075 | 3/2002 |
| WO | WO 03/057000 | 7/2003 |

\* cited by examiner

*Primary Examiner*—Long V Le
*Assistant Examiner*—Vani Gupta
(74) *Attorney, Agent, or Firm*—H. Henry Koda; William L. Androlia

(57) ABSTRACT

An ultrasonic diagnostic apparatus according to the present invention comprises a plurality of transducer units which are two-dimensionally arranged to transmit/receive an ultrasonic wave to/from hard tissue; a transceiver unit which receives an echo signal for each transducer unit from the plurality of transducer units; a surface point specifying unit which specifies a surface point corresponding to a surface of the hard tissue for each echo signal; and a form data generator unit which generates form data of hard tissue surface on the basis of a plurality of surface points obtained two-dimensionally from the echo signals of the plurality of transducer units.

14 Claims, 5 Drawing Sheets

| | BEFORE LOADING: TRANSLATION COMPONENT | BEFORE LOADING: ROTATION COMPONENT | AFTER LOADING: TRANSLATION COMPONENT | AFTER LOADING: ROTATION COMPONENT | CHANGE BEFORE AND AFTER LOADING: TRANSLATIONAL DISPLACEMENT COMPONENT | CHANGE BEFORE AND AFTER LOADING: ROTATION DISPLACEMENT COMPONENT |
|---|---|---|---|---|---|---|
| PROXIMAL SIDE (BONE FRACTURE 52a) | $Y_p$ | $\alpha_p, \beta_p, \gamma_p$ | $Y'_p$ | $\alpha'_p, \beta'_p, \gamma'_p$ | $\Delta Y_p = Y'_p - Y_p$ | $\Delta \alpha_p = \alpha'_p - \alpha_p$ <br> $\Delta \beta_p = \beta'_p - \beta_p$ <br> $\Delta \gamma_p = \gamma'_p - \gamma_p$ |
| DISTAL SIDE (BONE FRACTURE 52b) | $Y_d$ | $\alpha_d, \beta_d, \gamma_d$ | $Y'_d$ | $\alpha'_d, \beta'_d, \gamma'_d$ | $\Delta Y_d = Y'_d - Y_d$ | $\Delta \alpha_d = \alpha'_d - \alpha_d$ <br> $\Delta \beta_d = \beta'_d - \beta_d$ <br> $\Delta \gamma_d = \gamma'_d - \gamma_d$ |
| DIFFERENCE BETWEEN PROXIMAL SIDE AND DISTAL SIDE | $\delta Y = Y_p - Y_d$ | $\delta \alpha = \alpha_p - \alpha_d$ <br> $\delta \beta = \beta_p - \beta_d$ <br> $\delta \gamma = \gamma_p - \gamma_d$ | $\delta Y' = Y'_p - Y'_d$ | $\delta \alpha' = \alpha'_p - \alpha'_d$ <br> $\delta \beta' = \beta'_p - \beta'_d$ <br> $\delta \gamma' = \gamma'_p - \gamma'_d$ | $\delta \Delta Y = \Delta Y_p - \Delta Y_d$ | $\delta \Delta \alpha = \Delta \alpha_p - \Delta \alpha_d$ <br> $\delta \Delta \beta = \Delta \beta_p - \Delta \beta_d$ <br> $\delta \Delta \gamma = \Delta \gamma_p - \Delta \gamma_d$ |

Fig. 6

ULTRASONIC DIAGNOSTIC APPARATUS

BACKGROUND

1. Technical Field

The present invention relates to an ultrasonic diagnostic apparatus and in particular to an ultrasonic diagnostic apparatus which is used for diagnosis of hard tissue such as bone.

2. Related Art

Easy quantitative measurement of mechanical characteristics such as bone strength is desired for diagnosing bone metabolic diseases such as osteoporosis, judging fracture risk, and quantitatively diagnosing bone union after treatment of bone fracture.

The evaluation of bone formation and bone union depends largely on X-ray photography, but quantitatively diagnosing bone strength by means of X-ray photography is very difficult. As a conventional method of measuring bone strength there is known a strength test of a sample bone of a measurement target. However, this method requires an extraction operation for obtaining a sample bone, and thus, the method is invasive. A method of measuring an amount of bone and a bone density has employed devices such as X-ray CT and DXA (dual-energy x-ray absorptiometry). However, these devices are merely means for measuring the amount of bone and cannot provide an evaluation of bone strength. Moreover, in view that tissue is irradiated with X-rays in these methods, these methods cannot be considered non-invasive.

Other attempts to quantitatively evaluate bone strength include a strain gauge method in which a strain gauge is mounted on an external fixtator and the strain of the external fixtator is measured; a vibration wave method in which a vibration is applied to a bone from the outside and a characteristic frequency is evaluated; and an acoustic emission method in which acoustic waves generated by a bone which has reached yield stress are detected. These methods, however, have various problems in that a limitation is imposed on the treatment to which these methods can be applied, that the bone is subjected to invasion, and that evaluation precision is insufficient.

In view of the above circumstances, the inventors of the present application have proposed an ultrasonic diagnostic apparatus for noninvasively and quantitatively evaluating the mechanical characteristics of bone (Japanese Patent Laid-Open Publication No. 2004-298205).

The ultrasonic diagnostic apparatus described in Japanese Patent Laid-Open Publication No. 2004-298205 forms a plurality of ultrasonic beams on a bone, obtains a plurality of echo signals corresponding to the individual ultrasonic beams to specify a surface point corresponding to the bone surface for each echo signal, and generates shape data of the bone surface on the basis of the plurality of surface points obtained from the plurality of echo signals. Moreover, a mechanical characteristic of the bone is evaluated on the basis of a change in the shape data when an external load is applied to the bone. Thus, the apparatus is an epoch-making technology capable of noninvasively and quantitatively evaluating the mechanical characteristics of a bone in a living organism from the shape data of the bone surface on the basis of the echo signals.

The inventors of the present application have further improved the epoch-making technology described in Japanese Patent Laid-Open Publication No. 2004-298205 and have studied a method of more appropriately evaluating the mechanical characteristics and the like of hard tissue such as bone.

SUMMARY

The present invention has been conceived in view of the above circumstances and provides an ultrasonic diagnostic apparatus which enables highly accurate diagnosis of hard tissue such as bone.

To achieve the above object, an ultrasonic diagnostic apparatus according to one aspect of the invention comprises a plurality of transducer units which are two-dimensionally arranged to transmit/receive an ultrasonic wave to/from hard tissue; a transceiver unit which receives an echo signal for each transducer unit from the plurality of transducer units; a surface point specifying unit which specifies a surface point corresponding to a surface of the hard tissue for each echo signal; and a form data generator unit which generates form data of hard tissue surface on the basis of a plurality of surface points obtained two-dimensionally from the echo signals of the plurality of transducer units.

With such a structure, each transducer unit is configured of, for example, a single transducer element, and a plurality of transducer elements are arranged two-dimensionally. Of course, each transducer unit may be configured of a plurality of transducer elements. The plurality of transducer units are arranged, for example, in the shape of a lattice. Therefore, the surface points corresponding to the surface of the hard tissue can be obtained two-dimensionally, and it becomes possible to obtain two-dimensional form data regarding the hard tissue surface. The form data regarding the hard tissue surface are, for example, data such as the shape, position, orientation, and the like of the hard tissue surface. According to the above structure, the obtained form data regarding the hard tissue surface are two-dimensional, making it suitable for observation of, for example, a state of bone union, and the hard tissue such as bone can be diagnosed with higher precision.

BRIEF DESCRIPTION OF THE DRAWINGS

Embodiments of the present invention will be described in detail with reference to the following figures, wherein:

FIG. 6 is a diagram for explaining form data which can be obtained by means of two probes.

DETAILED DESCRIPTION

Embodiments of the present invention will now be described by reference to the figures.

Figure 1:
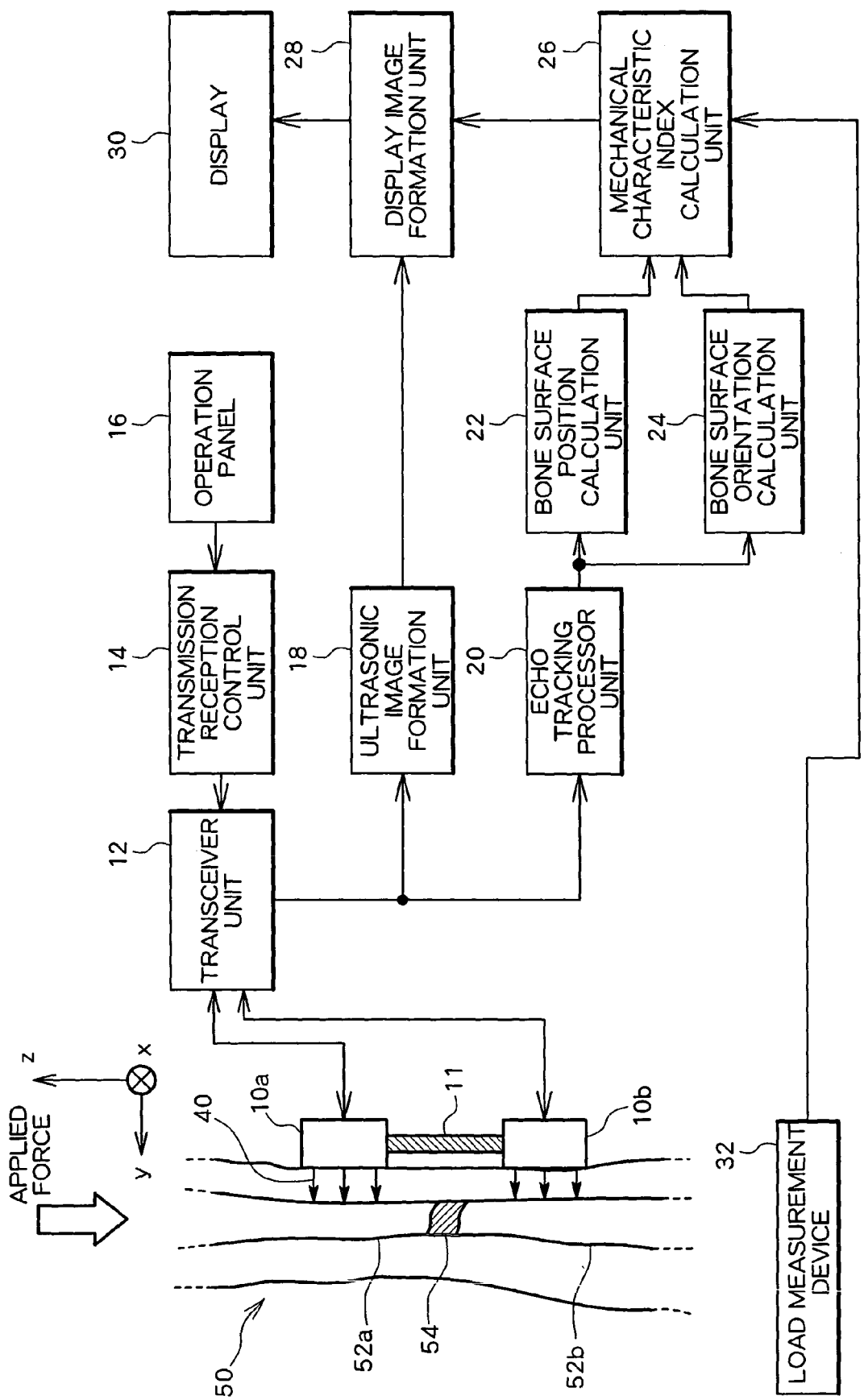
FIG. 1 is a block diagram showing an overall structure of an ultrasonic diagnostic apparatus according to the present invention.

FIG. 1 shows a preferred embodiment of the ultrasonic diagnostic apparatus according to the present invention. FIG. 1 is a block diagram showing overall structure of the apparatus.

In this embodiment, a probe 10a and a probe 10b are ultrasonic probes used while in contact with a surface of the body of a subject 50. Alternatively, an ultrasonic probe which is inserted into the subject may be used. The probe 10a and the probe 10b each transmit and receive a plurality of ultrasonic beams 40 to and from a bone (reference numerals 52a, 52b, 54) within the body of the subject 50. The bone is formed of two bone fragments 52a, 52b with a fractured portion 54 therebetween. The bone to be observed in this embodiment is, for example, the tibia. Of course, a bone other than the tibia or hard tissue other than bone may be observed. Also, the probe 10a and the probe 10b are mutually fixed by way of a probe connector 11. Specifically, relative positions and orientations between the probe 10a and the probe 10b are fixed.

In this embodiment, an ultrasonic wave is transmitted/received to/from the bone fragment 52a by the probe 10a, and an ultrasonic wave is transmitted/received to/from the bone fragment 52b by the probe 10b. The probe 10a and the probe 10b are provided with a plurality of transducers which are arranged two-dimensionally. In this embodiment, each of the probe 10a and the probe 10b is provided with a group of transducers which have a total of nine transducers arranged in the shape of a lattice, three in the vertical and horizontal directions, respectively. The arranged state of the nine transducers will be described later with reference to FIG. 4.

A transceiver unit 12 forms the plurality of ultrasonic beams 40 transmitted and received by the probe 10a and the probe 10b on the basis of the control effected by a transmission/reception control unit 14 and obtains a plurality of echo signals corresponding to the individual ultrasonic beams 40. The ultrasonic beams 40 are formed for each transducer. In this embodiment, three ultrasonic beams 40 are formed for the probe 10a, and three ultrasonic beams 40 are formed for the probe 10b. In this case, the probe 10a and the probe 10b each use three among the nine transducers to form the three ultrasonic beams 40 corresponding to the three transducers.

FIG. 1 shows only the ultrasonic beams 40 required for calculation of form data regarding the bone surface, but, for example, at least either the probe 10a or the probe 10b may be provided with a transmission/reception function for forming an ultrasonic image such as a B mode image or a three-dimensional image to obtain echo data, which is required for the ultrasonic image, by the transceiver unit 12 and to form image data according to the obtained echo data by an ultrasonic image formation unit 18. In this case, the formed image data are sent to a display image formation unit 28, and an ultrasonic image (a B mode image, a three-dimensional image or the like) corresponding to the image data is shown on a display 30.

The echo signal for calculating form data obtained in the transceiver unit 12, or the echo signal obtained from the ultrasonic beams 40 shown in FIG. 1, is output to an echo tracking processor unit 20. The echo tracking processor unit 20 performs a so-called echo tracking process in which bone surface sections are extracted from echo signals corresponding to the individual probe 10a and probe 10b to thereby perform tracking. For the echo tracking process, for example, a technique detailed in Japanese Patent Laid-Open Publication No. 2001-309918 is used.

For the echo tracking process, for example, an examiner inputs an instruction related to transmission/reception of the ultrasonic wave through an operation panel 16 to the transmission/reception control unit 14, and the transmission/reception control unit 14 controls the transceiver unit 12 on the basis of the instruction from the examiner. The ultrasonic beams 40 for obtaining tracking echo signals are transmitted to a diagnosis site on the bone surface according to the instruction from the examiner. In the transmission/reception of the ultrasonic wave, a strong reflected wave is obtained from the bone surface. Therefore, the echo signals obtained from within the body of the diagnosis target (subject) are obtained as having large amplitude in a portion corresponding to the bone surface.

Figure 2:
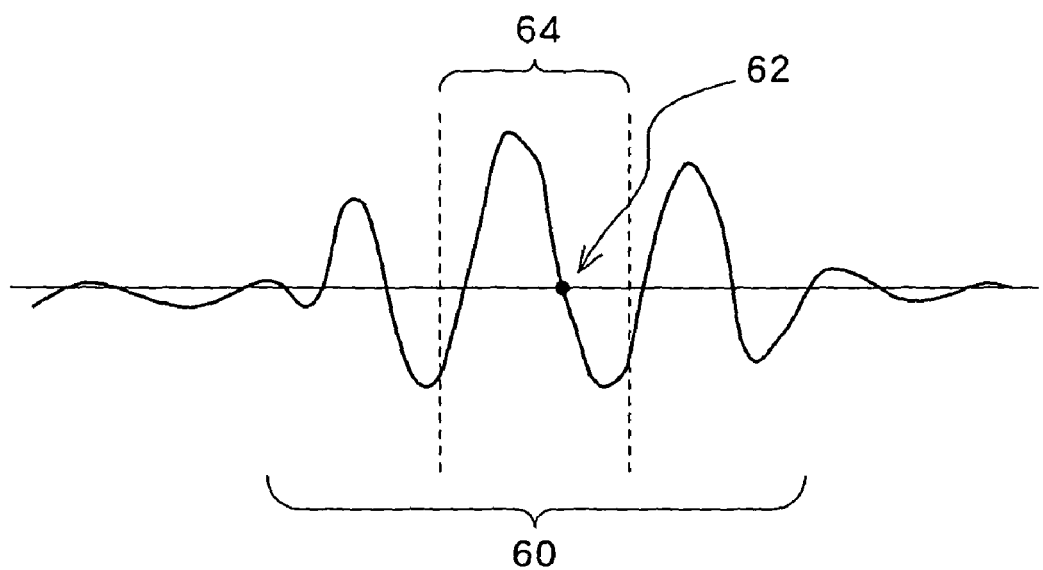
FIG. 2 is a diagram schematically showing an echo signal of a bone surface.

FIG. 2 is a diagram schematically showing a bone surface section of an echo signal. As shown in FIG. 2, each echo signal includes a range 60 within which the echo signal has a large amplitude corresponding to the bone surface. When the bone surface section is considered simply as a portion having a large amplitude, it is unclear as to which portion within the range 60 corresponds to the surface section and, as a result, there is an error approximately equal to the range 60. In the echo tracking process, a zero-cross point 62 is detected as a representative of each echo signal, and the detected zero-cross point 62 is tracked so as to significantly increase the precision of the bone surface position.

The zero-cross point 62 is detected as a time, within a tracking gate period 64, at which the polarity of the echo signal is inverted from positive to negative or from negative to positive. In FIG. 2, the zero-cross point 62 is a time at which the polarity of the echo signal is inverted from positive to negative. When the zero-cross point 62 is detected, a new tracking gate is set with the detected zero-cross point 62 as its center. In the echo signal obtained next, a zero-cross point 62 is detected within the newly set tracking gate period 64. In this manner, a zero-cross point 62 is tracked as the surface point for each echo signal. The surface point is tracked continuously from the measuring time before the load is applied until the measuring time after the load is applied through a process in which the load is applied.

Referring again to FIG. 1, the surface point is tracked by the echo tracking processor unit 20 for each echo signal; namely, for echo signals of three ultrasonic beams 40 corresponding to the probe 10a and for echo signals of three ultrasonic beams 40 corresponding to the probe 10b. As a result, three bone surface points of the bone fragment 52a and three bone surface points of the bone fragment 52b are extracted.

By reference to the extracted bone surface points, a bone surface position calculation unit 22 calculates position data on each of the bone fragment 52a and the bone fragment 52b. Meanwhile, by reference to the extracted bone surface points, a bone surface orientation calculation unit 24 calculates orientation(direction) data regarding each of the bone fragment 52a and the bone fragment 52b.

By reference to FIG. 3 through FIG. 5, a principle of calculating the form data (position data and orientation data) which are calculated by the bone surface position calculation unit 22 and the bone surface orientation calculation unit 24 will be described. In the following description, the reference numerals shown in FIG. 1 are assigned to the corresponding portions.

Figure 3:
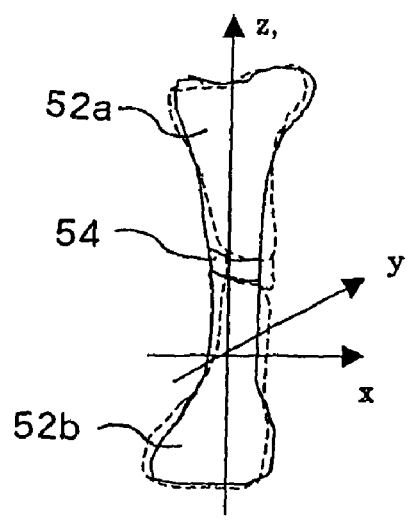
FIG. 3 is a diagram for explaining a bone fracture model used to calculate form data.

FIG. 3 is a diagram for explaining a bone fracture model used to calculate form data in this embodiment. In this embodiment, a composite model of a rigid body and a viscoelastic body is used as the bone fracture model. When the two bone fragments 52a, 52b (existing bones) having the fractured portion 54 ("callus" in the process of bone healing) therebetween receive a load such as a weight, they change, for example, from a state indicated by a solid line to a state indicated by a broken line in FIG. 3. Deformation of the two bone fragments 52a, 52b due to the load is very small, whereas deformation of the fractured portion 54 due to the load is relatively large. Accordingly, there is used a composite model which comprises the two bone fragments 52a, 52b formed of a rigid body and the fractured portion 54 formed of a viscoelastic body.

When the bone fragments 52a, 52b are assumed to be rigid bodies, the displacement of each bone fragment can be considered a translation component of a general reference position (e.g., displacement of a center-of-gravity point of the bone fragments as a whole and a rotation component around the reference position. When both the translation component and the rotation component are considered to be in a three-dimensional space, degrees of freedom of the translation component and the rotation component become 6 degrees of freedom in total. In other words, the bone fracture model shown in FIG. 3 has a degree of freedom (DOF) of 6 for each bone fragment.

In the bone fracture model shown in FIG. 3, with each of the probe 10a and the probe 10b taken as a reference, the direction of the ultrasonic beams 40 is designated a y axis, and an arrangement direction, which is substantially perpendicular to a longitudinal axis of the bone in the arrangement directions of the transducers which are arranged in the shape of a lattice, is taken as an x axis. Also, in the arrangement directions of the transducers arranged in the shape of a lattice, an arrangement direction which is perpendicular to the x axis is taken as a z axis. These x, y, and z axes are orthogonal to one another (the relation of arrangement of the three axes is also shown in FIG. 1). The probe 10a and the probe 10b are in contact with the surface of the subject such that the z axis is substantially aligned with the longitudinal axis of the bone. The above bone fracture model and coordinate system are used to describe a principle of calculating the form data.

Figure 4:
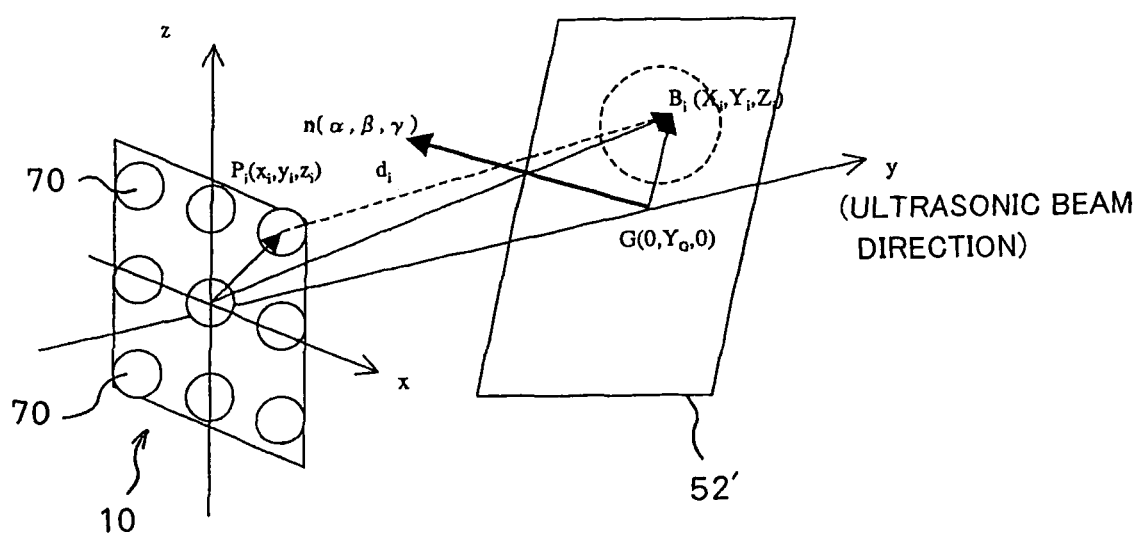
FIG. 4 is a diagram for explaining one of two probes and a surface of a corresponding bone fragment.

FIG. 4 is a diagram showing one of the two probes and a surface of its corresponding bone fragment. In other words, FIG. 4 corresponds to the probe 10a and the surface of the bone fragment 52a in FIG. 1, or the probe 10b and the surface of the bone fragment 52b. In FIG. 4, a probe 10 and a surface 52' of the bone fragment will be described.

The probe 10 has a group of transducers in which nine transducers 70 are arranged in the shape of a lattice. In other words, a total of nine transducers 70, three in each of the x-axis direction and the z-axis direction, are arranged in the shape of a lattice. The individual transducers 70 form the ultrasonic beams in the y-axis direction.

A spatial coordinate of an i-th transducer 70 is designated $P_i(x_i, y_i, z_i)$. A plurality of transducers 70 are disposed in the same xz plane, and a center-of-gravity point of the plurality of transducers 70 is defined as the origin of the xz plane. In other words, coordinate values $x_G$ and $z_G$ in the xz plane of the center-of-gravity point of the plurality of transducers 70 are defined as indicated by the following expression.

$$x_G = \frac{1}{M}\sum_i^M x_i = 0$$ [Expression 1]

$$z_G = \frac{1}{M}\sum_i^M z_i = 0.$$

Here, M denotes a quantity of the transducers 70 and is 9 (M=9) in this embodiment.

When a distance to position $B_i(X_i, Y_i, Z_i)$ of the surface 52' of the bone fragment measured by the i-th transducer 70 is taken as $d_i$, the following relation is established.

$X_i = x_i$ $Y_i = y_i + d_i, i = 1, 2, \ldots M$ $Z_i = z_i$ [Expression 2]

The center-of-gravity point of the measured value of the bone surface position by M transducers 70 is calculated by the following expression, and it is determined as the center-of-gravity point of the bone surface.

$$Y_G = \frac{1}{M}\sum_i^M Y_i$$ [Expression 3]

$$X_G = Z_G = 0$$

Then, under the assumption that a movement (translational displacement) of the center-of-gravity point of the bone surface is limited to the direction of the ultrasonic beams; namely, the y-axis direction, a degree of freedom of the bone fragment becomes 4 degrees of freedom including 1 degree of freedom in translation and 3 degrees of freedom in rotation. Also, the surface 52' of the bone fragment is assumed to be a plane within a range to be observed. When the normal vector of the plane is denoted vector n, and its direction cosine is denoted by (cos α, cos β, cos γ), the following relation is established with position $B_i(X_i, Y_i, Z_i)$ of the surface 52' of the bone fragment.

$\cos \alpha \cdot X_i + \cos \beta \cdot (Y_i - Y_G) + \cos \gamma \cdot Z_i = 0, i = 1, 2, \ldots M$ [Expression 4]

Here, $X_i$ and $Z_i$ are determined in a stage of designing the probe 10 in a geometrical arrangement of the transducers 70 and are known at the time of measurement. Moreover, $Y_i$ can be measured with high precision by the echo tracking process in this embodiment, and center-of-gravity point $Y_G$ is determined from expression 3. In other words, three values of angles α, β, γ become unknown numbers. Therefore, the number of measured data points of the position $B_i(X_i, Y_i, Z_i)$ of the surface 52' of the bone fragment is determined to be three (M=3), so that, in principle, three values of the angles α, β, γ are determined. The three transducers 70 for obtaining the three measured data points are desirably three transducers 70 which are not arranged on the same straight line. The number of measured data may be larger than three, and the three values of the angles α, β, γ may be determined by a least-squares method or the like.

According to the above method, the bone surface position calculation unit 22 calculates a y coordinate value $Y_G$ of the center-of-gravity point of the bone surface, and the bone surface orientation calculation unit 24 calculates the orientation (angles α, β, γ) of the bone surface.

In addition, in this embodiment, an external action (load) is applied to the bone by stamping or the like, and a change in center-of-gravity point of the bone surface and a change in orientation of the bone surface are measured. In other words, the center-of-gravity point of the bone surface is assumed to be $Y_G$, and the orientation of the bone surface is assumed to be angles α, β, γ before the application of the load, and after the application of the load, the center-of-gravity point of the bone surface is assumed to be $Y'_G$, and the orientation of the bone surface is assumed to be angles α', β', γ'. From the above values, a translational displacement component (position displacement data) and a rotational displacement component (orientation displacement data) are calculated as indicated by the following expression.

Translational Displacement Component:

$\Delta Y_G = Y'_G - Y_G$

Rotational Displacement Element:

$\Delta \alpha = \alpha' - \alpha$ $$\Delta\beta = \beta' - \beta$$

$$\Delta\gamma = \gamma' - \gamma \quad \text{[Expression 5]}$$

Instead of the translational displacement component and the rotational displacement component, a change in normal vector defined by the following expression may be determined from the normal vector (vector n) of the bone surface before the application of the load and the normal vector (vector n') of the bone surface after the application of the load.

$$\Delta \vec{n} = \vec{n}' - \vec{n} \quad \text{[Expression 6]}$$
$$= (\cos\tilde{\alpha}' - \cos\tilde{\alpha}, \cos\tilde{\beta}' - \cos\tilde{\beta}, \cos\tilde{\gamma}' - \cos\tilde{\gamma})$$
$$\vec{n}' = VECTORn', \vec{n}: VECTORn$$

Additionally, data which can be obtained through the two probes can be compared in this embodiment.

Figure 5:
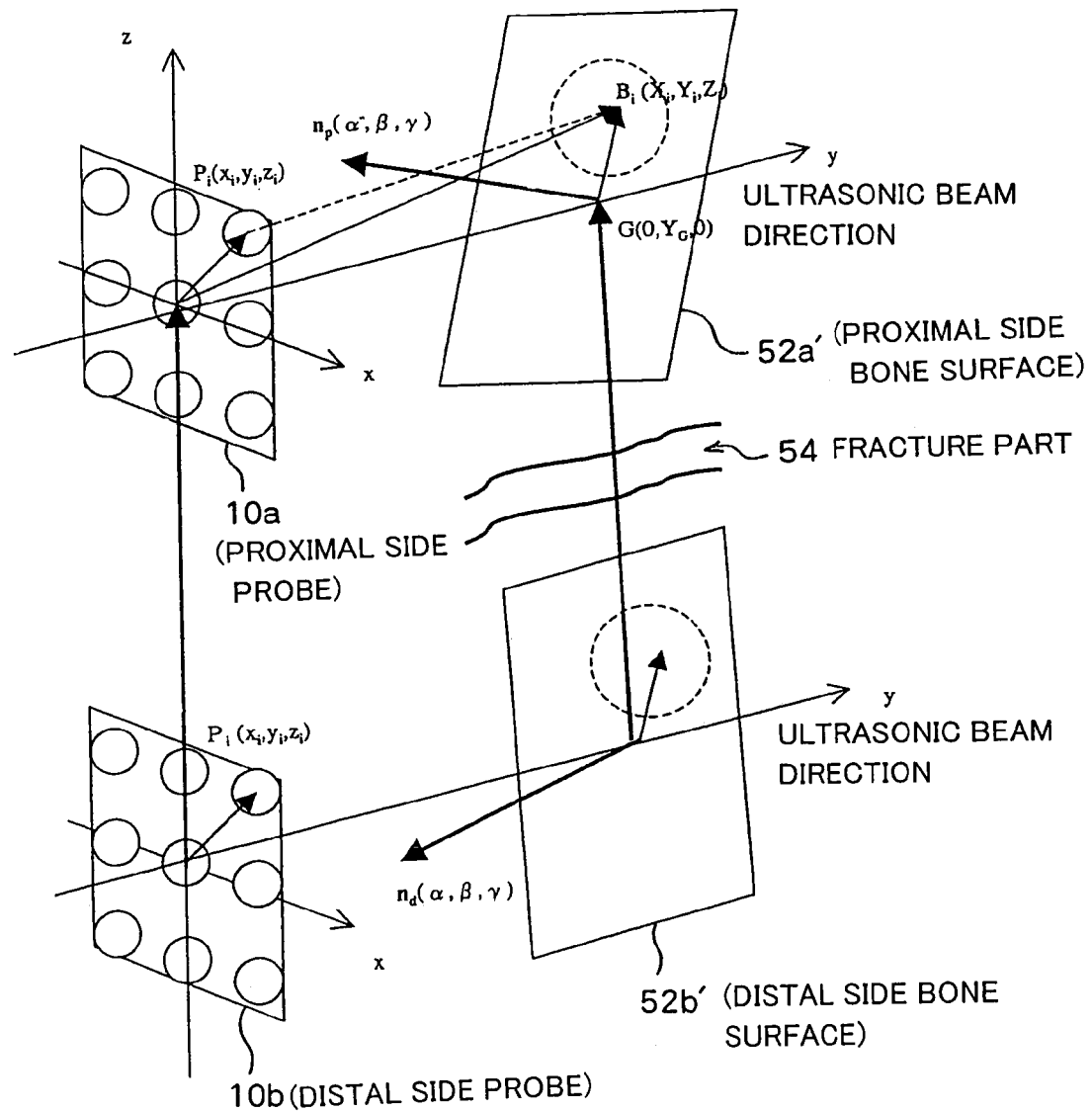
FIG. 5 is a diagram showing two probes and surfaces of corresponding bone fragments.

FIG. 5 is a diagram showing two probes and surfaces of the corresponding bone fragments. Specifically, the figure shows a bone fragment surface 52a' on a proximal side and the corresponding probe 10a (proximal side probe), and a bone fragment surface 52b' on a distal side and the corresponding probe 10b (distal side probe). The two bone fragments with the fractured portion 54 therebetween are measured.

In FIG. 5, the bone fracture model and the coordinate system shown in FIG. 3 are used. In other words, a composite model of a rigid body and a viscoelastic body are used as the bone fracture model, and an xyz orthogonal coordinate system having the probe as its origin is used. The two probes 10a and probe 10b are fixed by means of a rigid body or the like such that their z-axes are aligned with each other and are taped to a surface of the body of a patient.

For the bone fragment surface 52a' and the bone fragment surface 52b', the y coordinate value $Y_G$ of the center-of-gravity point of the bone surface and the orientation (angles $\alpha$, $\beta$, $\gamma$) of the bone surface are calculated by the calculation technique described with reference to FIG. 4. A difference between the states before and after the application of the load is calculated as the translational displacement component and the rotational displacement component. In addition, comparison data (difference between the proximal side and the distal side) of the two bone fragments of the bone fragment surface 52a' nd the bone fragment surface 52b' are determined in FIG. 5.

FIG. 6 is a diagram explaining form data which can be obtained through the two probes shown in FIG. 5, showing a table including the form data. The table of FIG. 6 will be described with the reference numerals of FIG. 5 assigned to the corresponding portions.

In data related to the bone (bone fragment 52a) on the proximal side obtained through the probe 10a, the translation component $Y_P$ before the application of the load corresponds to the center-of-gravity point $Y_G$ which can be obtained for the bone fragment 52a from expression 3. Rotation components $\alpha_P$, $\beta_P$, $\gamma_P$ before the application of the load correspond to the angles $\alpha$, $\beta$, $\gamma$ obtained for the bone fragment 52a from expression 4. The translation component and the rotation component can also be obtained after the application of the load, and they are translation component $Y'_P$ after the application of the load and rotation components $\alpha'_P$, $\beta'_P$, $\gamma'_P$ after the application of the load. In addition, translational displacement component $\Delta Y_P$ is calculated as a difference in translation component before and after the application of the load, and rotational displacement components $\Delta\alpha_P$, $\Delta\beta_P$, $\Delta\gamma_P$ are calculated as a difference in rotation component before and after the application of the load. Instead of the translational displacement component and the rotational displacement component, a change in normal vector may be obtained from normal vector (vector $n_P$) of the bone surface before and after the application of the load.

For the bone (bone fragment 52b) on the distal side obtained through the probe 10b, the same data as that related to the bone (bone fragment 52a) on the proximal side can be obtained. In other words, the translation component and the rotation component before the application of the load, the translation component and the rotation component after the application of the load, the translational displacement component, and the rotational displacement component are determined. These distal side data are appended with a subscript d.

In FIG. 6, a difference between the proximal side and the distal side is determined as comparison data of two bone fragments. In other words, there are determined a difference $\delta Y$ between the proximal side and the distal side of the translation component before the application of the load, differences $\delta\alpha$, $\delta\beta$, $\delta\gamma$ between the proximal side and the distal side of the rotation component before the application of the load, a difference $\delta Y'$ between the proximal side and the distal side of the translation component after the application of the load, differences $\delta\alpha'$, $\delta\beta'$, $\delta\gamma'$ between the proximal side and the distal side of the rotation component after the application of the load, a difference $\delta\Delta Y$ between the proximal side and the distal side of the translational displacement component, and differences $\delta\Delta\alpha$, $\delta\Delta\beta$, $\delta\Delta\gamma$ between the proximal side and the distal side of the rotational displacement component.

Thus, comparison data of the surfaces (surface 52a' and surface 52b') of the two bone fragments having the fractured portion 54 therebetween is obtained and used as data effective for the comprehensive high-precision diagnosis of the entire bone including the two bone fragments having the fractured portion 54 therebetween.

For example, in a case where a tibia is measured, a walking excise (stepping exercise) can be used as a load to be applied to the bone. Various data before the application of the load shown in FIG. 6 are determined before walking, and then various data after the application of the load are determined after lapse of a prescribed time (e.g., about one minute) after walking. In this case, changes in the translational displacement component and the rotational displacement component before and after the application of the load are used as quantitative data of, for example, bone plastic deformation.

Thus, the data obtained through the two probes can be compared in this embodiment.

Referring again to FIG. 1, when form data (data shown in FIG. 6) related to the bone are obtained in the bone surface position calculation unit 22 and the bone surface orientation calculation unit 24, these form data are output to a mechanical characteristic index calculation unit 26.

The mechanical characteristic index calculation unit 26 calculates an index value of the mechanical characteristics of the bone on the basis of the form data related to the bone obtained from the bone surface position calculation unit 22 and the bone surface orientation calculation unit 24 and the measured value of the load applied to the bone obtained from a load measurement device 32. For example, hysteresis characteristics of the bone and the like are determined from the measured values of the load obtained from the load measurement device 32 and the translational displacement component and rotational displacement component obtained for the individual measured value of the load. In addition, evaluated values of viscoelasticity and the like of the bone may be calculated from the determined hysteresis characteristics and the like. The load measurement device 32 is suitably a force plate or the like for the walking exercise.

The display image formation unit 28 forms a display image on the basis of an ultrasonic image formed by the ultrasonic image formation unit 18 and an index value determined by the mechanical characteristic index calculation unit 26 and shows it on the display 30. For example, the ultrasonic image and the index value are alternately shown according to an instruction by the examiner. The ultrasonic image and the index value may be shown at the same time. As the index value, the form data (in part or all) shown in FIG. 6 may be shown on the display 30.

As described above, the index value of the mechanical characteristics of the bone obtained according to the form data is expected to be an important index for quantitative evaluation and the like of bone union. For example, in a case where it is judged from the index value that plastic deformation is very large, the bone is considered to be in the initial stage of a healing process. Therefore, the load for promotion of the bone union is restricted. Meanwhile, in a case where it is judged from the index value that plastic deformation is small, a relatively heavy load may be recommended for promotion of the bone union. In other words, the form data become very effective data when the patient is given an instruction about a degree of load. Where the plastic deformation is small, a larger load may be applied to judge the plastic deformation.

The form data and the index value which can be obtained by the ultrasonic diagnostic apparatus of this embodiment make significant contributions as objective and reliable base data for diagnosis in judgment of effects of an agent on an increase in the bone strength, removal of a fixtator/implant, and the like.

An embodiment of the present invention has been described above, but the invention may have the following embodiments.

The ultrasonic diagnostic apparatus which is one aspect of the present invention comprises a plurality of transducer units which are two-dimensionally arranged to transmit/receive an ultrasonic wave to/from hard tissue; a transceiver unit which receives an echo signal for each transducer unit from the plurality of transducer units; a surface point specifying unit which specifies a surface point corresponding to a surface of the hard tissue for each echo signal; and a form data generator unit which generates form data of hard tissue surface on the basis of a plurality of surface points obtained two-dimensionally from the echo signals of the plurality of transducer units, wherein the form data generator unit generates position data indicating a general position of the hard tissue surface on the basis of the plurality of surface points obtained two-dimensionally as the form data.

In a desired aspect, the form data generator unit generates orientation data indicating an orientation of the hard tissue surface on the basis of the plurality of surface points obtained two-dimensionally as the form data. In a desired aspect, an external action is applied to the hard tissue, and the form data generator unit generates position displacement data indicating a change in general position of the hard tissue surface involved in the external action, and orientation displacement data indicating a change in orientation of the hard tissue surface involved in the external action as the form data.

In a desired aspect, the surface point specifying unit uses a tracking gate which is set for ultrasonic beams formed for the individual transducer units, extracts as a surface point a representative point of an echo signal within a tracking gate period, and performs tracking of the extracted surface point. In a desired aspect, the plurality of transducer units include three transducer units which are not arranged on the same straight line, and the form data generator unit determines on the basis of three surface points obtained from the three transducer units a coordinate of a center-of-gravity position of the three surface points as the position data, and further determines a normal vector of a plane including the three surface points as the orientation data.

An ultrasonic diagnostic apparatus according to one aspect of the present invention comprises a first probe which is provided with a plurality of transducers for transmission/reception of an ultrasonic wave to/from a first bone fragment between two bone fragments with a fractured portion therebetween and has the plurality of transducers arranged two-dimensionally; a second probe which is provided with a plurality of transducers for transmission/reception of an ultrasonic wave to/from a second bone fragment between the two bone fragments and has the plurality of transducers arranged two-dimensionally; a transceiver unit which obtains an echo signal for each transducer from the plurality of transducers of the first probe and further obtains an echo signal for each transducer from the plurality of transducers of the second probe; a surface point specifying unit which specifies a surface point corresponding to a surface of a bone for the each echo signal for each of the first bone fragment and the second bone fragment; and a form data generator unit which generates form data of a surface of the first bone fragment on the basis of the plurality of surface points obtained two-dimensionally from echo signals of the plurality of transducers of the first probe, and further generates form data of a surface of the second bone fragment on the basis of the plurality of surface points obtained two-dimensionally from echo signals of the plurality of transducers of the second probe.

In a preferable embodiment, the first probe and the second probe are mutually fixed, and the form data generator unit generates comparison data between form data of the first bone fragment and form data of the second bone fragment. In a preferable embodiment, an external action is applied to the two bone fragments, and the form data generator unit determines first displacement data indicating a change in form data of the first bone fragment involved in the external action, and second displacement data indicating a change in form data of the second bone fragment involved in the external action. In a preferable embodiment, the form data generator unit generates displacement comparison data by comparing the first displacement data and the second displacement data.

In a preferable embodiment, the form data generator unit generates, as form data of the first bone fragment, position data indicating a general position of the surface of the first bone fragment on the basis of the plurality of surface points obtained through the first probe, and generates, as form data of the second bone fragment, position data indicating a general position of the surface of the second bone fragment on the basis of the plurality of surface points obtained through the second probe.

In a preferable aspect, an external action is applied to the two bone fragments, and the form data generator unit determines first displacement data indicating a change in position data of the first bone fragment involved in the external action, and second displacement data indicating a change in position data of the second bone fragment involved in the external action. In a preferable aspect, the form data generator unit generates displacement comparison data by comparing the first displacement data and the second displacement data.

In a preferable aspect, the form data generator unit generates, as form data of the first bone fragment, orientation data indicating an orientation of a surface of the first bone fragment on the basis of the plurality of surface points obtained through the first probe, and generates, as form data of the second bone fragment, orientation data indicating an orientation of a surface of the second bone fragment on the basis of the plurality of surface points obtained through the second probe.

In a preferable aspect, an external action is applied to the two bone fragments, and the form data generator unit determines first displacement data indicating a change in orientation data of the first bone fragment involved in the external action, and second displacement data indicating a change in orientation data of the second bone fragment involved in the external action. In a preferable aspect, the form data generator unit generates displacement comparison data by comparing the first displacement data and the second displacement data.

It should be noted that embodiments of the present invention described above are provided for illustration only and do not limit the scope of the present invention.

The invention claimed is:

1. An ultrasonic diagnostic apparatus comprising:
a plurality of transducer units which are two-dimensionally arranged to transmit/receive an ultrasonic wave to/from a bone fragment of a bone including a fractured portion and the bone fragment;
a transceiver unit which forms an ultrasonic beam and receives an echo signal for each of the transducer units from the plurality of transducer units;
a surface point specifying unit which specifies, for each ultrasonic beam, a surface point corresponding to a bone surface based on the echo signal corresponding to the ultrasonic beam;
an echo tracking processing unit which performs tracking of the surface point on the ultrasonic beam; and
a form data generator unit which generates form data of the bone on the basis of a plurality of surface points obtained two-dimensionally from a plurality of ultrasonic beams corresponding to the plurality of transducer units; wherein
the form data generator unit uses a composite model wherein the two bone fragments are a rigid body and the fractured portion is a viscoelastic body as a bone fracture model to generate as the form data position data indicating a general position era surface of the bone fragment and orientation data indicating an orientation of the surface of the bone fragment on the basis of the plurality of surface points obtained two-dimensionally; and
the form data generator unit determines using said composite model first displacement data indicates a change in position data of the first bone fragment involved in the external action, and second displacement data indicating a change in position data of the second bone fragment involved in the external action.

2. The ultrasonic diagnostic apparatus according to claim 1, wherein:
the form data generator unit generates position displacement data indicating a change of the position data involved in the external action.

3. The ultrasonic diagnostic apparatus according to claim 2, wherein:
the form data generator unit generates orientation displacement data indicating a change of the orientation data involved in the external action.

4. The ultrasonic diagnostic apparatus according to claim 3, wherein:
the echo tracking processor unit uses a tracking gate which is set for ultrasonic beams formed for the individual transducer units, extracts as a surface point a representative point of an echo signal within a tracking gate period, and performs tracking of the extracted surface point.

5. The ultrasonic diagnostic apparatus claim 4, wherein:
the plurality of transducer units include three transducer units which are not arranged on a same straight line, and
the form data generator unit determines on the basis of three surface points obtained from the three transducer units a coordinate of a center-of-gravity position of the three surface points as the position data, and further determines as the orientation data a normal vector of a plane including the three surface points.

6. An ultrasonic diagnostic apparatus comprising:
a first probe which is provided with a plurality of transducers for transmission/reception of an ultrasonic wave to/from a first bond fragment between two bone fragments with a fractured portion therebetween, the plurality of transducers being arranged two-dimensionally;
a second probe which is provided with a plurality of transducers for transmission/reception of an ultrasonic wave to/from a second bone fragment between the two bone fragments, the plurality of transducers being arranged two-dimensionally;
a probe coupling unit which mutually fixes the first probe and the second probe;
a transceiver unit which obtains an echo signal for each transducer from the plurality of transducers of the first probe and further obtains an echo signal for each transducer from the plurality of transducers of the second probe;
a surface point specifying unit which specifies a surface point corresponding to a surface of a bone for the each echo signal for each of the first bone fragment and the second bone fragment; and
a form data generator unit which generates form data of a surface of the first fragment on the basis of the plurality of surface points obtained two-dimensionally from echo signals of the plurality of transducers of the first probe, and further generates form data of a surface of the second fragment on the basis of the plurality of surface points obtained two-dimensionally from echo signals of the plurality of transducers of the second probe, wherein
the form data generator unit uses a composite model in which the two bone wherein the two bone fragments are a rigid body and the fractured portion is a viscoelastic body as a bone fracture model to generate the form data;
an external action is applied to the two bone fragments, and
the form data generator unit determines using said composite model first displacement data indicates a change in position data of the first bone fragment involved in the external action, and second displacement data indicating a change in position data of the second bone fragment involved in the external action.

7. The ultrasonic diagnostic apparatus according to claim 6, wherein:
the form data generator unit generates displacement comparison data by comparing the first displacement data and the second displacement data.

8. The ultrasonic diagnostic apparatus according to claim 6, wherein:
the form data generator unit generates, as form data of the first bone fragment, position data indicating a general position of the surface of the first bone fragment on the basis of the plurality of surface points obtained through the first probe, and generates, as form data of the second bone fragment, position data indicating a general position of the surface of the second bone fragment on the basis of the plurality of surface points obtained from the second probe.

9. The ultrasonic diagnostic apparatus according to claim 8, wherein:
an external action is applied to the two bone fragments, and
the form data generator unit determines first displacement data indicating a change in position data of the first bone fragment involved in the external action, and second displacement data indicating a change in position data of the second bone fragment involved in the external action.

10. The ultrasonic diagnostic apparatus according to claim 9, wherein:
the form data generator unit generates displacement comparison data by comparing the first displacement data and the second displacement data.

11. The ultrasonic diagnostic apparatus according to claim 6, wherein:
the form data generator unit generates, as form data of the first bone fragment, orientation data indicating an orientation of a surface of the first bone fragment on the basis of the plurality of surface points obtained through the first probe, and generates, as form data of the second bone fragment, orientation data indicating an orientation of a surface of the second bone fragment on the basis of the plurality of surface points obtained through the second probe.

12. The ultrasonic diagnostic apparatus according to claim 11, wherein:
an external action is applied to the two bone fragments, and
the form data generator unit determines first displacement data indicating a change in orientation data of the first bone fragment involved in the external action, and second displacement data indicating a change in orientation data of the second bone fragment involved in the external action.

13. The ultrasonic diagnostic apparatus according to claim 12, wherein:
the form data generator unit generates displacement comparison data by comparing the first displacement data and the second displacement data.

14. The ultrasonic diagnostic apparatus according to claim 6, wherein said form data generator unit generates two different sets of form data from echo signals of the first and second probe whereby a condition of the hard tissue is obtained.

* * * * *